(12) United States Patent
Takada et al.

(10) Patent No.: US 6,525,054 B1
(45) Date of Patent: Feb. 25, 2003

(54) CYANOIMINOQUINOXALINE DERIVATIVES

(75) Inventors: Susumu Takada, Kawanishi (JP); Nobuo Chomei, Osaka (JP); Tsuyoshi Kihara, Toyonaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/701,383

(22) PCT Filed: May 28, 1999

(86) PCT No.: PCT/JP99/02822

§ 371 (c)(1),
(2), (4) Date: Dec. 1, 2000

(87) PCT Pub. No.: WO99/62887

PCT Pub. Date: Dec. 9, 1999

(30) Foreign Application Priority Data

Jun. 1, 1998 (JP) ............................................. 10-151017

(51) Int. Cl.$^7$ ..................... C07D 241/44; A61K 31/495
(52) U.S. Cl. ........................ 514/248; 514/249; 544/354; 544/356
(58) Field of Search .................................. 544/354, 356; 514/248, 249

(56) References Cited

U.S. PATENT DOCUMENTS

| 5,677,305 A | 10/1997 | Takada et al. ............... 514/249 |
| 6,369,057 B1 | 4/2002 | Billhardt et al. ......... 514/234.8 |

FOREIGN PATENT DOCUMENTS

| WO | 96/10023 | 4/1996 |
| WO | WO 97/19934 | 6/1997 |
| WO | 97/32585 | 7/1997 |
| WO | WO 97/32858 | 9/1997 |

OTHER PUBLICATIONS

Aspey et al. (Metab. Brain Dis. 12(3): 237–49) PubMed Abstract, Sep. 1997.*
Iijima (Masui, 47(6): 662–77) PubMed Abstract Jun. 1998.*
During et al., An Oral Vaccine Against NMDAR1 with Efficacy in Experimental Stroke and Epilepsy, Science, vol. 287, pp. 1453–1460, Feb. 2000.*
C.S. Chapleo, et al., Journal of Medicinal Chemistry, vol. 25, No. 7, pp. 821–824, "Synthesis of Some Potential Antihypertensive Phthalazinyl– And Quinoxalinylguanidines," 1982.

* cited by examiner

*Primary Examiner*—Deepak Rao
(74) *Attorney, Agent, or Firm*—Oblon, Spivak, McClelland, Maier & Neustadt, P.C.

(57) ABSTRACT

A cyanoiminoquinoxaline derivative of the formula (II) is useful as a preventive or therapeutic agent for diseases due to hyperexcitation of glutamate receptors.

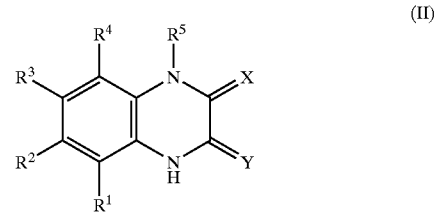

(II)

(wherein, X and Y each is independently O or NCN, provided that at least one of X and Y is NCN; $R^1$, $R^2$, $R^3$, and $R^4$ each is independently hydrogen, halogen, nitro, optionally substituted heterocyclic group etc.; $R^5$ is hydrogen etc.; $R^1$ and $R^2$, $R^2$ and $R^3$, $R^3$ and $R^4$, and $R^4$ and $R^5$, each taken together with the adjacent atoms may form a carbocycle which may be substituted or may contain a heteroatom(s).)

25 Claims, No Drawings

CYANOIMINOQUINOXALINE DERIVATIVES

The present application is a 371 of PCT/JP99/02822 filed on May 28, 1999, which was not published in English under PCT article 21(2), which in turn claims priority to Japanese Patent Application 10-151017 filed Jun. 1, 1998.

TECHNICAL FIELD

The present invention relates to novel cyanoiminoquinoxaline derivatives possessing antagonistic effects on glutamate receptors of central neurons, in particular, NMDA receptors and AMPA receptors.

BACKGROUND ART

Amino acids such as L-glutamic acid and L-aspartic acid are indispensable as neurotransmitters for activating neurons in the central nervous system. However, excess accumulation of these excitatory amino acids surrounding neurons is considered to induce hyperexcitation of neurons, causing neurological disorders such as Parkinsonism, senile dementia, Huntington's disease, and epilepsy; and hyponoia and hypokinesis found after ischemia, anoxia, hypoglycemia, or head and spinal cord trauma (see, McGeer et al. Nature, 263, 517–519 (1976); Simon et al. Science, 226, 850–852 (1984), Wieloch, Science, 230, 681–683 (1985); Faden et al. Science, 244, 798–800 (1989); Turski et al. Nature, 349, 414–418 (1991)).

It has been known that the above-mentioned excitatory amino acids act on the central nervous system neurons via a glutamate receptor on the neurons. Thus, compounds competitively inhibiting the binding of the excitatory amino acids to such a receptor have been considered to be useful as therapeutic or preventive reagents for the above-mentioned diseases and conditions such as antiepileptic, ischemic encephalopathy, and Parkinsonism.

The above-mentioned glutamate receptors can be classified into two groups: an ion channel type and a metabolism type. The ion channel type is further classified into three groups based on its selectivity with respect to binding to the agonist. These three are called N-methyl-D-aspartate (NMDA) receptors, 2-amino-3-(3-hydroxy-5-methylisoxazol-4-yl)propanoate (AMPA) receptors, and kainate receptors.

The NMDA receptors are selectively activated by agonists such as NMDA and ibotenic acid. Hyperexcitation of the NMDA receptors allows a large amount of calcium ions to flow into neurons, which has been considered one of the causes for the death of neurons. Hithertofore, as antagonists selectively binding to the NMDA receptors, D-2-amino-5-phosphovalerate (D-AP5), 3-[2-carboxypiperazin-4-yl] propyl-1-phosphate (CPP), and the like are known. Further reported is that the NMDA receptors have an allosteric site bound to glycine as well as a site recognizing the above-mentioned agonists, and that the binding of the allosteric site to glycine remarkably enhances the functions of the NMDA receptors. Examples of antagonists to the glycine-binding sites include e.g., 5,7-dichlorokynurenic acid and HA966 (Eur. J. Pharmacol., 151 161–163 (1988)).

The AMPA receptors are selectively activated by agonists such as AMPA, glutamic acid, and quisqualic acid. Examples of the antagonits to the AMPA receptors include compounds having a quinoxaline structure, particularly quinoxaline-2,3-dione derivatives such as 6,7-dinitroquinoxaline-2,3-dione (DNQX), 6-cyano-7-nitroquinoxaline-2,3-dione (CNQX), 2,3-dihydroxy-6-nitro-7-sulfamoylbenzoquinoxaline (NBQX), and 6-imidazolyl-7-nitroquinoxaline-2,3-(1H, 4H)-dione (YM900), 6,7-dichloro-8-nitro-1,4-dihydroxyquinoxaline-2, 3-dione (ACEA1021) (Science,241, 701–703(1988), Eur.J.Pharmacol.,174, 197–204(1989), WO92/07847, JP-A 63-83074, JP-A 63-258466, JP-A 1-153680, JP-A 2-48578, JP-A 2-221263, JP-A 2-221264, Exp. Opin. Ther. Patents (1997) 7 (10), etc.).

Further, compounds to be used as therapeutic agents effective against the above-mentioned diseases and disorders, protecting neurons from death or denaturation caused by the excitatory amino acids, are required to effectively work as antagonists to both of the NMDA receptors and the AMPA receptors (Mosinger et al., Exp. Neurol., 113 10–17 (1991)). Examples of such compounds include quinoxaline-2,3-dione derivatives having a 4-oxo-4H-pyridyl group at the 7-position (JP-A 7-324084, U.S. Pat. No. 5,677,305), quinoxaline-2,3-dione derivatives having an alkylsulfonylimino group at the 2-position (WO97/32858).

DISCLOSURE OF INVENTION

In general, most of the known excitatory amino acid antagonists, which have quinoxaline structures therein, precipitate in renal, uriniferou tubule or the like to show side-effects such as nephrotoxicity, as reported on NBQX for example (J. Cerb Blood Flow Metab., Vol. 14, No. 2 (1994)). Thus, the antagonists are difficult to develop and have not practically been utilized as medicines. Further, even if the side-effect could be inhibited to some extent, it was not always easy to maintain the pharmacological effect on the level applicable to clinical use. Accordingly, it has been desired to develop a novel glutamate receptor antagonist which has a quinoxaline structure and can be administered safely to human.

The present inventors have intensively studied to find out that novel quinoxaline derivatives possess potent antagonistic effects on glutamate receptors without side-effects such as nephrotoxicity in the body. The finding is preferably characterized by the conversion of at least one of the oxo (=O) groups at the 2- and 3-positions into a cyanoimino (=NCN) group(s). Further, methods for preparing the present compounds and the intermediates thereof have been found out to accomplish the present invention shown below.

(1) a compound having a quinoxaline structure wherein at least one of the 2- and 3-positions is substituted with a cyanoimino group (hereinafter referred to as a cyanoiminoquinoxaline derivative of the present invention), (2) a compound described in above (1), which has, in the quinoxaline structure, a partial structure of the formula:

(I)

wherein X and Y each is independently O or NCN, provided that at least one of X and Y is NCN (hereinafter referred to as partial structure (I)), (3) a compound of the formula:

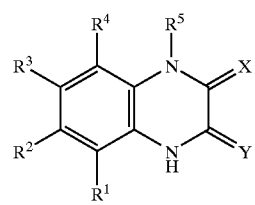

(II)

wherein,
X and Y each is independently O or NCN, provided that at least either X and Y is NCN;
$R^1$, $R^2$, $R^3$, and $R^4$ each is independently hydrogen, halogen, nitro, cyano, hydroxy, optionally substituted amino, optionally substituted lower alkyl, optionally substituted lower cycloalkyl, optionally substituted lower alkoxy, optionally substituted lower alkylthio, optionally substituted lower alkylcarbonyl, carbamoyl optionally substituted with lower alkyl, carbamoylamino optionally substituted with lower alkyl, sulfamoyl optionally substituted with lower alkyl, sulfamoylamino optionally substituted with lower alkyl, optionally substituted sulfonyl, optionally substituted aryl, optionally substituted heterocyclic group, or optionally substituted heterocyclylthio;
$R^5$ is hydrogen, hydroxy, optionally substituted lower alkyl, optionally substituted lower alkoxy, or optionally substituted lower cycloalkyl;
$R^1$ and $R^2$, $R^2$ and $R^3$, $R^3$ and $R^4$, and $R^4$ and $R^5$, each together with the atoms adjacent thereto may form a carbocycle which may be substituted or contain a heteroatom(s), the pharmaceutically acceptable salt, or the hydrate thereof (these hereinafter referred to as compound(II)),
(4) a compound (II) described in above (3), wherein X is NCN: Y is O,
(5) a compound (II) described in above (3), wherein X is O; Y is NCN,
(6) a compound (II) described in above (3), wherein both X and Y are NCN,
(7) a compound (II) described in above (3), wherein $R^5$ is hydrogen,
(8) a compound (II) described in above (3), wherein X is NCN; Y is O; $R^5$ is hydrogen,
(9) a compound (II) described in above (3), wherein $R^1$ is hydrogen, halogen, or nitro,
(10) a compound (II) described in above (3), wherein $R^2$ is hydrogen, halogen, nitro, or halogenated lower alkyl,
(11) a compound (II) described in above (3), wherein $R^3$ is hydrogen, halogen, nitro, halogenated lower alkyl, optionally substituted heterocyclic group, or optionally substituted heterocyclylthio,
(12) a compound (II) described in above (3), wherein $R^4$ is hydrogen, halogen, or nitro,
(13) a compound (II) described in above (3), wherein $R^1$ is hydrogen; $R^2$ is hydrogen, halogen, nitro, or halogenated lower alkyl; $R^3$ is hydrogen, halogen, nitro, halogenated lower alkyl, optionally substituted heterocyclic group, or optionally substituted heterocyclylthio; $R^4$ is hydrogen, halogen, or nitro,
(14) a compound (II) described in above (3), wherein X is NCN; Y is O; $R^1$ is hydrogen; $R^2$ is hydrogen, halogen, nitro, or halogenated lower alkyl; $R^3$ is hydrogen, halogen, nitro, halogenated lower alkyl, optionally substituted heterocyclic group, or optionally substituted heterocyclylthio; $R^4$ is hydrogen, halogen, or nitro; $R^5$ is hydrogen,
(15) a compound (II) described in above (3), wherein X is NCN; Y is O; $R^1$ is hydrogen; $R^2$ is halogen, nitro, or trihalogenated methyl; $R^3$ is halogen, nitro, trihalogenated methyl, optionally substituted heterocyclic group, or optionally substituted heterocyclylthio; $R^4$ is hydrogen or nitro; $R^5$ is hydrogen,
(16) a compound (II) described in any one of above (13)–(15), wherein optionally substituted heterocyclic group is 1,4-dihydro-4-oxo-1-pyridyl, 1-imidazolyl or 1-pyrrolyl; heterocyclylthio is 2-imidazolylthio,
(17) a compound (II) described in above (3), wherein X is NCN; Y is O; $R^1$ is hydrogen; $R^2$ is nitro; $R^3$ is 4-oxo-1-pyridyl; $R^4$ is hydrogen; $R^5$ is hydrogen,
(18) a compound described in above (17), which is a monosodium salt of 2-cyanoimino-1,4-dihydro-7-(1,4-dihydro-4-oxo-1-pyridyl)-6-nitro-3-quinoxaline,
(19) a compound described in any one of above (1)–(18), which has an antagonistic effect on glutamate receptors without substantially showing nephrotoxicity upon administration into the body,
(20) a pharmaceutical composition containing a compound described in any one of above (1)–(19),
(21) a pharmaceutical composition having an antagonistic effect on glutamate receptors, which contains a compound described in any one of above (1)–(19),
(22) a pharmaceutical composition for preventing or treating diseases due to hyperexcitation of glutamate receptors, which contains a compound described in any one of above (1)–(19),
(23) a pharmaceutical composition described in above (22), wherein the disease due to hyperexcitation of glutamate receptors is stroke,
(24) a method for preventing or treating diseases due to hyperexcitation of glutamate receptors, which comprises administering a compound described in any one of above (1)–(19),
(25) use of a compound described in any one of above (1)–(19) for preparing a medicament for preventing or treating diseases due to hyperexcitation of glutamate receptors,
(26) a method for preparing a compound (II) of the formula:

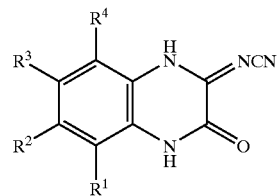

(II-1)

wherein $R^1$, $R^2$, $R^3$ and $R^4$ are the same as defined above, which comprises
1) dealkylating "$R^6$" portion of a compound (III-1) of the formula:

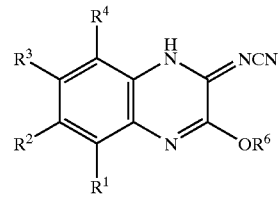

(III-1)

wherein $R^1$, $R^2$, $R^3$ and $R^4$ are the same as defined above; $R^6$ is a hydroxy protecting group, or 2) hydrolyzing "Hal" portion of a compound (IV-1) of the formula:

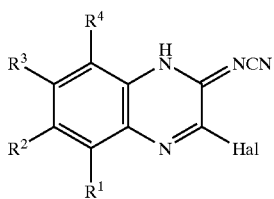

(IV-1)

wherein $R^1$, $R^2$, $R^3$ and $R^4$ are the same as defined above; Hal is halogen.

(27) a compound (III-1) or compound (IV-1) described in above (26).

A Cyanoiminoquinoxaline derivative of the present invention means a variety of bi-, tri- or more-cyclic condensed compounds having a quinoxaline structure, wherein at least one of carbon atoms at the 2- and 3-positions is substituted with a cyanoimino group. When only one of the 2- and 3-positions is substituted with cyanoimino, the other is not substituted or substituted with a group such as oxo, halogen, cyano, hydroxy, lower alkoxy (e.g., methoxy, ethoxy, i-propoxy, and tert-butoxy), or carboxyl, alkylsulfonylamino (e.g., methylsulfonylamino).

In a preferred embodiment, a cyanoiminoquinoxaline derivative of the present invention has the above-described partial structure (I) in the quinoxaline structure. In such a case, two N atoms in the partial structure (I) are located at the 1- and 4-positions of quinoxaline. The structure other than the partial structure (I) is a di- or tri-valent group which taken together with the two N atoms can form a condensed ring of ten or more members, and preferred is an optionally substituted divalent benzene ring group.

A cyanoiminoquinoxaline derivative of the present invention is preferably the above-described compound (II). Each substituent of the compound (II) is explained below.

Examples of halogen include F, Cl, Br, and I.

Examples of lower alkyl include straight or branched C1–C6 alkyl, such as methyl, ethyl, i-propyl, tert-butyl, pentyl, and hexyl. Preferred is C1–C4 alkyl.

Examples of lower cycloalkyl include C3–C6 cycloalkyl, such as cyclopropyl, cyclobutyl, cyclopentyl, and cyclohexyl.

Examples of lower alkoxy include oxy bonding to the above-described lower alkyl, such as methoxy, ethoxy, i-propoxy, tert-butoxy, pentyloxy, and hexyloxy.

Examples of lower alkylthio include thio bonding to the above-described lower alkyl, such as methylthio, ethylthio, i-propylthio, tert-butylthio, pentylthio, and hexylthio.

Examples of lower alkylcarbonyl include carbonyl bonding to the above-described lower alkyl, such as methylcarbonyl, ethylcarbonyl, i-propylcarbonyl, tert-butylcarbonyl, pentylcarbonyl, and hexylcarbonyl.

Each substituent on amino, lower alkyl, lower cycloalkyl, lower alkoxy, lower alkylthio, or lower alkylcarbonyl is optionally selected from the group consisting of lower alkyl (e.g., methyl, ethyl, propyl, and butyl), lower alkylcarbonyl (e.g., acetyl), lower alkoxycarbonyl (e.g., methoxycarbonyl and ethoxycarbonyl), lower alkoxycarbonylmethyl (e.g., methoxycarbonylmethyl), halogen (e.g., F, Cl, Br, and I), halogenated lower alkyl (esp., trihalogenated methyl (e.g., $CF_3$), optionally substituted amino (e.g., dimethylamino, diethylamino, and benzoylamino), cyano, nitro, carboxy, oxo, carboxymethyl, CHO, $PO(OH)_2$, $OPO(OH)_2$, $PO(OCH_2CH_3)_2$, $SO_3H$, $SO_2CH_3$, $SO_2CF_3$ optionally substituted phenyl (e.g., phenyl, p-nitrophenyl, p-methylphenyl, and m-chlorophenyl), carbamoyl optionally substituted with lower alkyl (e.g., carbamoyl and methylcarbamoyl), sulfamoyl optionally substituted with lower alkyl (e.g., sulfamoyl, methylsulfamoyl), optionally substituted acylamino (e.g., thienylacetylamino), heterocyclic group (e.g., pyrrolidinyl, thiophenyl, imidazolyl, tetrazolyl, morpholinyl), phenylaminocarbonyl, and benzoylaminoethyl.

Examples of substituents on sulfonyl include lower alkyl (e.g., methyl, ethyl, propyl, and butyl), aryl (e.g., phenyl and naphthyl), and heterocyclic group (e.g., pyrrolidinyl, thiophenyl, imidazolyl, tetrazolyl, and morpholinyl).

Examples of aryl include phenyl and naphthyl.

Examples of heterocyclic group include a 5- to 7-membered aromatic or non-aromatic cyclic group containing 1 to 4, same or different, heteroatom(s) selected from the group consisting of O, S, and N. In the light of pharmacological activity, preferred is a 5- to 6-membered cyclic group containing N atom, such as pyridyl, imidazolyl, triazolyl, pyrrolyl, and piperidyl, and more preferred is 1,4-dihydro-1-pyridyl, 1-imidazolyl, and 1-pyrrolyl.

Examples of heterocyclylthio include thio bonding to the above-described heterocyclic group, such as pyridylthio, imidazolylthio, triazolylthio, pyrrolylthio, and piperidylthio, and preferred is 2-imidazolylthio.

Examples of each substituent on the above-described aryl, heterocyclic group, or heterocyclylthio include 1 to 4 group (s) optionally selected from the group consisting of oxo, thioxo, halogen, nitro, cyano, amino, acylamino (e.g., acetylamino, benzoylamino, and pyridylcarbonylamino), acylaminomethyl (e.g., acetylaminomethyl), di(lower) alkylamino (e.g., dimethylamino), carboxy, lower alkyl (e.g., methyl and ethyl), halogenated lower alkyl (e.g., trifluoromethyl), carboxy lower alkyl (e.g., carboxymethyl), lower alkoxy (e.g., methoxy and ethoxy), halogenated lower alkoxy (e.g., trifluoromethoxy), lower alkoxycarbonyl (e.g., methoxycarbonyl), lower alkoxymethyl (e.g., methoxymethyl), lower alkoxycarbonylmethyl (e.g., methoxycarbonylmethyl), carbamoyl optionally substituted with lower alkyl (e.g., methylcarbamoyl), carbamoylamino optionally substituted with lower alkyl (e.g., methylcarbamoylamino), sulfamoylamino optionally substituted with lower alkyl (e.g., methylsulfamoylamino), $SO_3H$, $SO_2NH_2$, $NHCSNH_2$, NHCSH, $NHSO_2NH$, $NHSO_2CF_3$, optionally substituted aryl (e.g., halogenated phenyl), pyridylcarbamoylmethyl, piperazinylcarbonyl, and heterocyclic group (e.g., pyridyl), and preferred is oxo.

Examples of "carbocycle containing a hetero atom(s)" which is formed by any combination of $R^1$ and $R^2$, $R^2$ and $R^3$, $R^3$ and $R^4$, and $R^4$ and $R^5$, together with the adjacent atoms, include a 5- to 7-membered ring which may contain 1 to 4, same or different, hetero atom(s) selected from the group consisting of O, S, and N, such as benzene, thiophen, pyrrole, pyrrolidine, imidazole, oxazole, thiazole, imidazoline, imidazolidine, oxazolidine, pyridine, pyran, thiopyran, piperidine, piperadine, morphorino, and triazole. These groups may have a substitute(s) similar to those mentioned as to the above-described heterocyclic group.

Preferred examples of each group are shown below.

X and Y is preferably NCN and O, respectively.

$R^1$ is preferably hydrogen, halogen, nitro, methylsulfonylamino, (N-carboxymethyl)methylsulfonylamino, more preferably hydrogen, halogen, or nitro, and particularly hydrogen.

$R^2$ is preferably hydrogen, halogen, nitro, halogenated lower alkyl (e.g., trifluoromethyl), cyano, carboxyl, lower alkyl (e.g., methyl), lower alkoxy (e.g., methoxy), halogenated lower alkoxy (e.g., trifluoromethoxy), lower alkylthio (e.g., methylthio), halogenated lower alkylthio (e.g., trifluoromethylthio), di-lower alkylamino (e.g., dimethylamino), optionally substituted aryl (e.g., 4-chlorophenyl), optionally substituted heterocyclic group (e.g., 1,4-dihydro-4-oxo-1-pyridyl, 1-imidazolyl, 1-pyrrolyl, and 3-carboxy-1-pyrrolyl), optionally substituted heterocyclylthio, lower alkylsulfonyl (e.g., methylsulfonyl), or lower alkylaminosulfonyl (e.g., methylaminosulfonyl), more preferably halogen (e.g., Cl), nitro, or trihalogenated methyl (e.g., trifluoromethyl), and particularly nitro.

$R^3$ is preferably hydrogen, halogen, nitro, halogenated lower alkyl(e.g., trifluoromethyl), cyano, lower alkyl (e.g., methyl), optionally substituted lower alkoxy (e.g., diethylaminoethoxy), halogenated lower alkoxy (e.g., trifluoromethoxy), lower alkylthio (e.g., methylthio), halogenated lower alkylthio (e.g., trifluoromethylthio), di-lower alkylamino (e.g., dimethylamino), (N-carboxymethyl)methylsulfonylamino, optionally substituted aryl (e.g., 4-chlorophenyl), optionally substituted heterocyclic group, optionally substituted heterocyclylthio, lower alkylsulfonyl (e.g., methylsulfonyl), or lower alkylaminosulfonyl (e.g., methylaminosulfonyl), and more preferably halogen (e.g., Cl), nitro, trihalogenatedmethyl (e.g., trifluoromethyl), optionally substituted heterocyclic group (e.g., 1,4-dihydro-4-oxo-1-pyridyl, 1-imidazolyl, 1-pyrrolyl, 3-carboxyl-pyrrolyl), or optionally substituted heterocyclylthio (e.g., 1-imidazolylthio), particularly 1,4-dihydro-4-oxo-1-pyridyl.

$R^4$ is preferably hydrogen, halogen, nitro, 5-methyl-1-tetrazolyl, 3-thienylacetylamino, dimethylaminomethyl, or pyrrolidinylmethyl, more preferably hydrogen, halogen, or nitro, and particularly hydrogen.

$R^5$ is preferably hydrogen, lower alkyl (e.g., methyl, ethyl, and propyl), carboxymethyl, —$CH_2PO(OEt)_2$, or —$CH_2PO(OH)_2$, more preferably hydrogen.

A cyanoiminoquinoxaline derivative of the present invention can be prepared through reactions well known to a parson skilled in the art. One of the representative methods is a process converting "oxo" to "cyanoimino" at the 2- and/or 3-position of quinoxaline-2,3-dione derivatives, which are known materials or easily synthesized by a person skilled in the art. Preferably, a cyanoimino group(s) can be introduced to the 2- and/or 3-position of a 1,4-dihydroquinoxaline-2,3-dione derivative, by halogenating the oxo parts at the 2- and 3-positions, followed by the reaction with 2 equivalents of cyanoiminating reagent. Otherwise, the introduction of a cyanoimino group(s) at the 2- and/or 3-position can be carried out by converting at least one of the halogens in advance, followed by the reaction with an equivalent of a cyanoiminating reagent. Further, the oxo atoms at the 2- and 3-positions can be converted to alkoxy groups, followed by changing any of $R^1$–$R^5$ groups to the other substituent(s), then an equivalent of a cyanoiminating reagent is used to introduce a cyanoimino group(s) at the 2- or 3-position. Further, the obtained cyanoiminoquinoxaline derivative can be chemically modified to give the other compound of the present invention. In the above-described processes, $R^1$–$R^5$ each can be converted to the other substituent, if necessary. General methods of compound (II) are shown below. The methods and all the novel intermediates thereof are encompassed in the present invention. Compound (III-1), compound (IV-1), or the like is useful as an intermediate for compound (II).

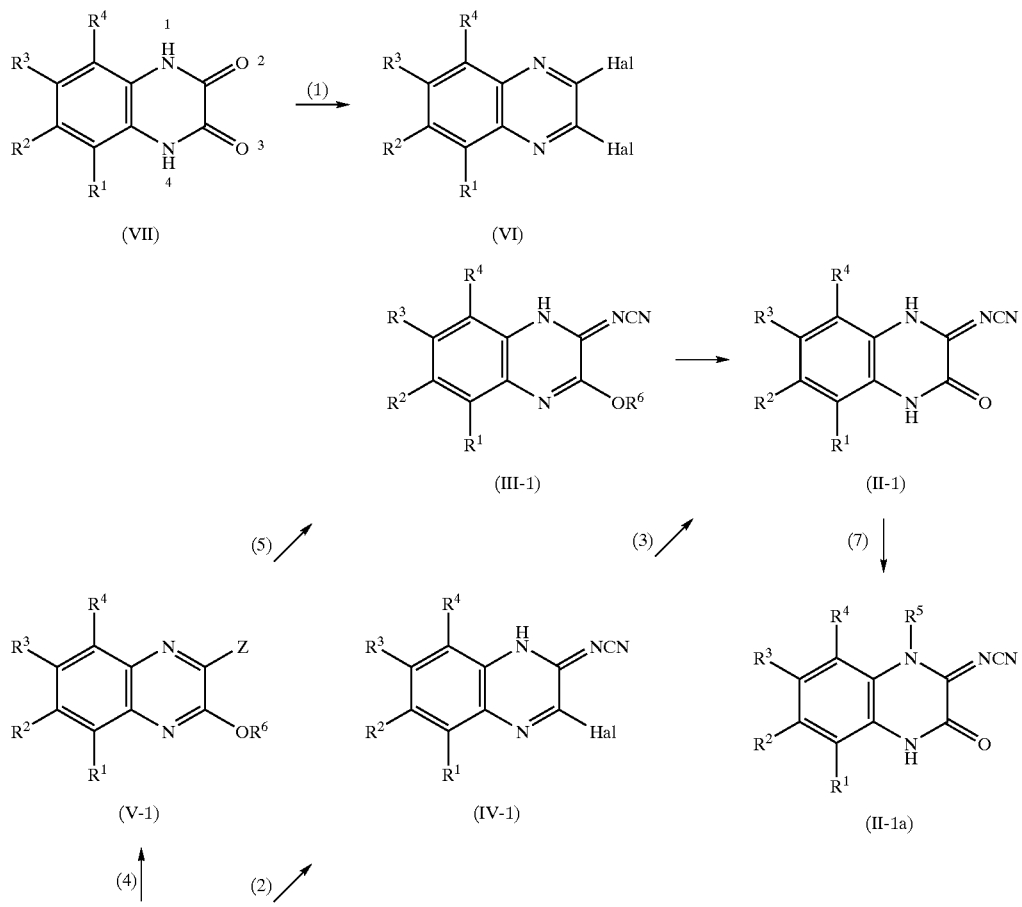

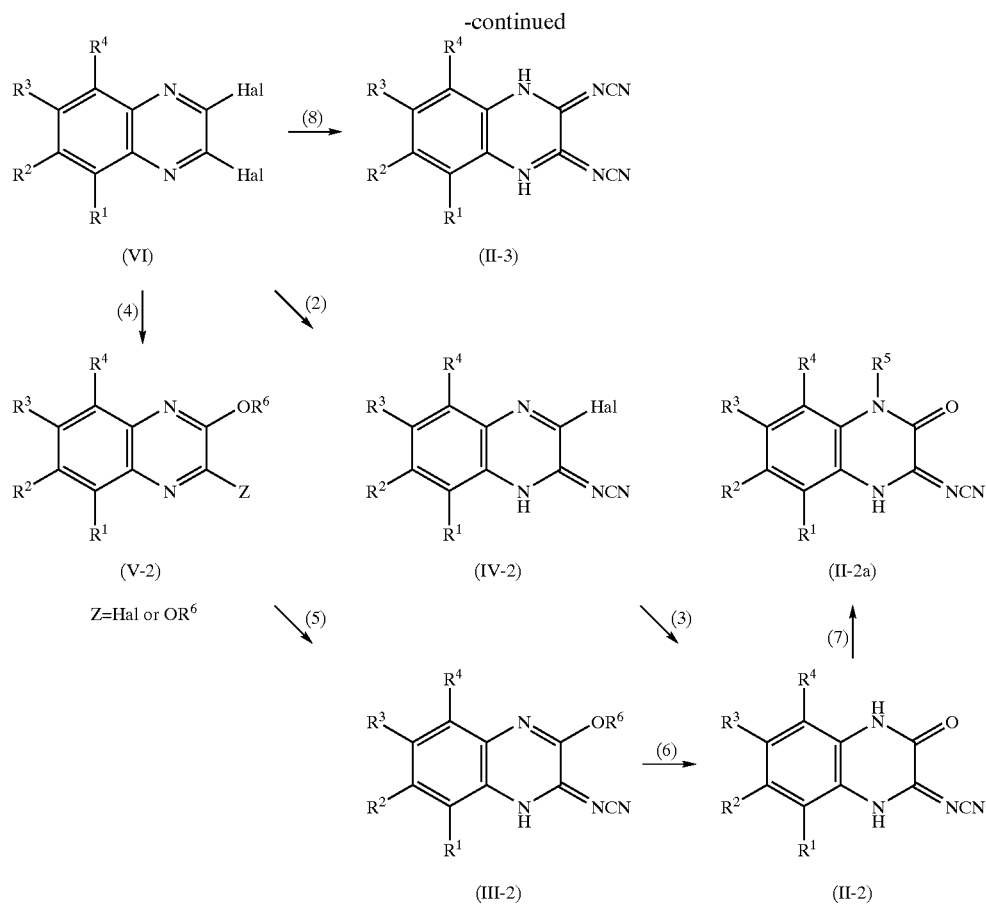

(1) Compound (VII)→Compound (VI)

Halogenation is carried out to oxo at the 2- and 3-positions of compound (VII), 1,4-dihydro-quinoxaline-2,3-dione derivative, according to the method well known to a person skilled in the art. Examples of the halogenating reagent include phosphorus oxychloride, thionyl chloride, phosphorus pentachloride, and phosphorus tribromide. A solvent may be used if necessary, such as benzene, toluene, N,N-dimethylaniline, methylene chloride, and chloroform. Further if necessary, a reaction accelerating reagent may used, such as DMF (N,N-dimethylformamide). The reaction temperature is usually about 0 to 200° C., preferably about 50 to 150° C.

Part of Compound (VII) is known in the above-described prior arts such as JP-A H07-324084, JP-A H08-59660, and WO97/32858, or the compound can be prepared according to the methods described therein. Some of compound (VI) are also described in WO97/32858. In the above-described reaction scheme, the position-numbering of the quinoxaline structure of compound (VII) is ruled as shown above for convenience, and the rule applies to the derivatives thereof.

(2) Compound (VI)→Compound (IV-1, IV-2)

Either halogen at the 2- and 3-positions of compound (VI) is converted into cyanoimino by the method well known to a person skilled in the art. Examples of the reagent include sodium hydride\cyanamide, monosodium cyanamide, and disodium cyanamide. Examples of the solvent include, DMF, DMSO (dimethylsulfoxide), N-methylpyrrolidone, and N,N-dimethylacetamide. The reaction temperature is usually about −20 to 50° C., preferably 0 to 20° C.

(3) Compound (IV-1, IV-2)→Compound (II-1, II-2)

Each halogen part of compound (IV-1) and (IV-2) is hydrolized converting it into oxo by the method well known to a person skilled in the art. Examples of the hydrolizing reagent include a base such as NaOH and KOH. Examples of the solvent include e.g., water and hydrated alcohol. The reaction temperature is usually about 0 to 80° C., preferably about 20 to 50° C.

(4) Compound (VI)→Compound (V-1,V-2)

Each halogen at the 2- and/or 3-position of compound (VI) is converted into a protected hydroxy by the method well known to a person skilled in the art. In the above reaction scheme, Z means halogen or $OR^6$ and $R^6$ is a hydroxy protecting group. Examples of the reagent include potassium t-butoxide, sodium methoxide, sodium ethoxide, sodium propoxide, sodium isopropoxide, and sodium benzyloxide. Examples of the solvent include t-BuOH, MeOH, EtOH, PrOH, i-PrOH, toluene, THF (tetrahydrofran), and DMF. The reaction temperature is usually about −20 to 50° C., preferably −10 to 20° C.

The hydroxy protecting group shown of $R^6$ is not particularly limited, and preferred is lower alkyl (e.g., methyl, ethyl, propyl, isopropyl, and tert-butyl), or benzyl.

(5) Compound (V-1,V-2)→Compound (III-1, III-2)

Z part (halogen or $OR^6$) of compound (V-1) or (V-2) is converted into cyanoimino by the method well known to a person skilled in the art. Examples of the reagent include sodium hydride/cyanamide, monosodium cyanamide, disodium and cyanamide. Examples of the solvent include DMF, DMSO, N-methylpyrrolidone, N,N-dimethylacetamide, and toluene. The reaction temperature is usually about −20 to 50° C., preferably −10 to 20° C.

(6) Compound (III-1, III-2)→Compound (II-1, II-2)

OR$^6$ of compound (III-1) or (III-2) is dealkylated to convert it into oxo by the methods well known to a person skilled in the art. In case of the de-alkylation under acidic conditions, examples of the reagent include acids such as hydrogen chloride, and trifluoroacetic acid; examples of the solvent include ethyl acetate, toluene, methylene chloride, and chloroform, and the reaction temperature is usually about −20 to 50° C., preferably −10 to 20° C. In case of the dealkylation under basic conditions, examples of the reagent include NaOH and KOH; examples of the solvent include water, DMSO, DMF, and N-methylpyrrolidone, and the reaction temperature is about 0 to 100° C., preferably about 20 to 80° C.

(7) Compound (II-1, II-2)→Compound (II-1a, II-2a)

$R^5$ is introduced to the 1-N-position of compound (II-1) or (II-2) by the method well known to a person skilled in the art. Examples of the reagent include various electrophilic reagents having the $R^5$ group, such as alkyl halide (e.g., MeI and EtBr), alkyl phosphonate (e.g., diethyl chloromethylphosphonate), and ethyl chloroacetate.

Examples of the solvent include THF and DMF. The reaction temperature is usually about 0 to 50° C., preferably about 0 to 20° C.

(8) Compound (VI)→Compound (II-3)

Both Halogens at the 2- and 3-positions of compound (VI) is converted into cyanoimino by the method well known to a person skilled in the art. Examples of the reagent include sodium hydride/cyanamide, monosodium cyanamide, and disodium cyanamide. Examples of the solvent include DMF, DMSO, N-methylpyrrolidone, and N,N-dimethylacetamide. The reaction temperature is usually about −20 to 50° C., preferably −10 to 20° C.

In the above-described reactions, appropriate protection to a functional group can be carried out in advance, and if necessary, the deprotection after the reaction(s), according to the method well known to a person skilled in the art.

Examples of salts of a cyanoiminoquinoxaline derivative of the present invention include various types which are formed with inorganic bases, ammonia, organic bases, inorganic acids, organic acids, basic amino acids, or halogen ion, and the inner salts. Examples of the inorganic bases include alkali metals (e.g., Na and K), alkaline-earth metals (e.g., Ca and Mg). Examples of the organic bases include trimethylamine, triethylamine, coline, procaine, and ethanolamine. Preferred is Na salts. Examples of the inorganic acids include hydrochloric acid, hydrobromic acid, sulfuric acid, nitric acid, and phosphoric acid. Examples of the organic acids include p-toluenesulfonic acid, methanesulfonic acid, formic acid, trifluoroacetate, and maleic acid. Examples of the basic amino acids include lysine, arginine, ornithine, and histidine. The derivatives of the present invention may be hydrates (e.g., dihydrate) or solvates.

A Cyanoiminoquinoxaline derivative of the present invention may be various kinds of steroisomers depending upon conditions, and all of the theoretically possibe steroisomers and mixtures thereof are included within the scope of the present invention. For example, compound (II) wherein $R^5$ is H may be in the equilibrium state shown below.

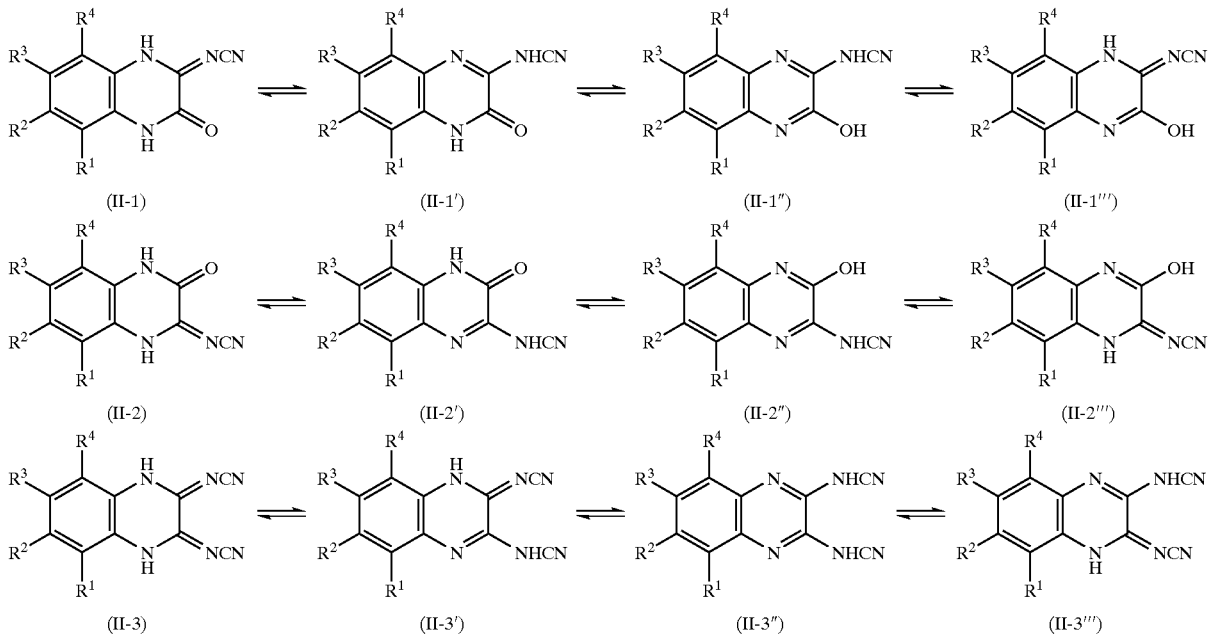

A Cyanoiminoquinoxaline derivative of the present invention can be a preventive or therapeutic agent for central nerve diseases caused by the binding of excitatory amino acids to the NMDA receptors, particularly to glycine-binding sites and AMPA receptors. Examples of the central nerve diseases include Parkinsonism, senile dementia, Huntington's disease, and epilepsy, cerebral infarction, stroke, ischemic cerebral disorder or the like.

A composition of the present invention is preferably an injectable solution or suspension, though it may be other formulations such as granules, tablets, and capsules. The composition may contain, if necessary, various additives such as physiologic saline, D-glucose, pH adjusting agents, disintegrating agents, solubilizing agents, excipients, and stablizers.

A compound of the present invention can be administered orally or parenterally, esp. intravenously, to humans. The dose may be varied depending upon the age, weight, and condition of patients, expected effects, or the administration route or time. In general, the dose for oral administration is about 1–1000 mg, preferably 10–500 mg; and for parenteral use it is about 1–500 mg, per an adult and a day. The compound can be administered in one to several divisions a day or continuously.

The present invention is explained in more detail by the following examples, which are not to limit the scope of the present invention.
(Abbreviation)
Me=methyl; Et=ethyl; ipr=isopropyl; t-Bu=tert-butyl; DMF=N,N-dimethylformamide; DMSO=dimethylsulfoxide

EXAMPLE 1

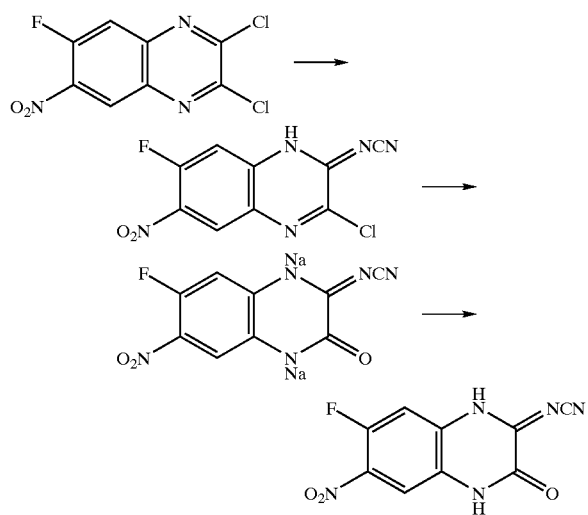

(1) 2-chloro-3-cyanoimino-6-fluoro-7-nitro-4H-quinoxaline

To a solution of cyanamide 2.31 g in DMF 100 mL, was added sodium hydride (60% suspension in oil) 4.40 g under ice-cooling. The mixture was stirred at room temperature for 30 min, to which 2,3-dichloro-6-fluoro-7-nitroquinoxaline 13.10 g was added under ice-cooling, followed by raising slowly to room temperature. The resulting mixture was stirred at room temperature for 20 min, then which was poured into ice water containing 1N HCl 110 mL under stirring. The precipitation was collected by filtration and washed with water and i-PrOH to give the title compound 12.80 g.

mp: 195–205° C. (decomp.)
$H^1$-NMR ($d_6$-DMSO) δ: 7.49 (1H, d, $J_{HF}$=12.8 Hz), 8.46 (1H, d, $J_{HF}$=8.0 Hz).

(2) 2-cyanoimino-1,4-dihydro-7-fluoro-6-nitro-3-quinoxaline disodium salt

2-Chloro-3-cyanoimino-6-fluoro-7-nitro-4H-quinoxaline 2.68 g obtained in the above-described (1) was added to 2N NaOH 50 mL and the mixture was stirred at 50° C. for 3 hr. The precipitated crystal was collected by filtration, washed with i-PrOH-water (4:1), i-PrOH, and i-PrO$_2$, and dried in vacuum, to give the title compound 2.33 g.

mp: >300° C.
$^1$H-NMR ($d_6$-DMSO) δ: 6.80 (1H, d, $J_{HF}$=14.2 Hz), 7.53 (1H, d, $J_{HF}$=8.2 Hz).

(3) 2-cyanoimino-1,4-dihydro-7-fluoro-6-nitro-3-quinoxaline

To a solution of the disodium salt (300 mg) of above (2) dissolved in water 3 mL, was added 1N HCl to adjust the pH to 4. The precipitation was collected by filtration, washed with water and methanol, and dried, to give the title compound 190 mg.

mp: 255–260° C. (decomp.)
Elementary analysis for $C_9H_4N_5O_3F$
Calcd.:C, 43.39; H, 1.62; N, 28.11; F, 7.62 (%).
Found:C, 43.18; H, 1.80; N, 27.71; F, 7.28 (%).
$^1$H-NM ($d_6$-DMSO) δ: 7.26 (1/2 H, br-d, $J_{HF}$=12.2 Hz), 7.85 (1/2 H, d, $J_{HF}$=7.4 Hz), 7.94 (1/2 H, d, $J_{HF}$=12.8 Hz), 8.65 (1/2 H, d, $J_{HF}$=7.8 Hz), 9.44 (3/2 H, br), 12.40 (1/2 H, br).

EXAMPLE 2

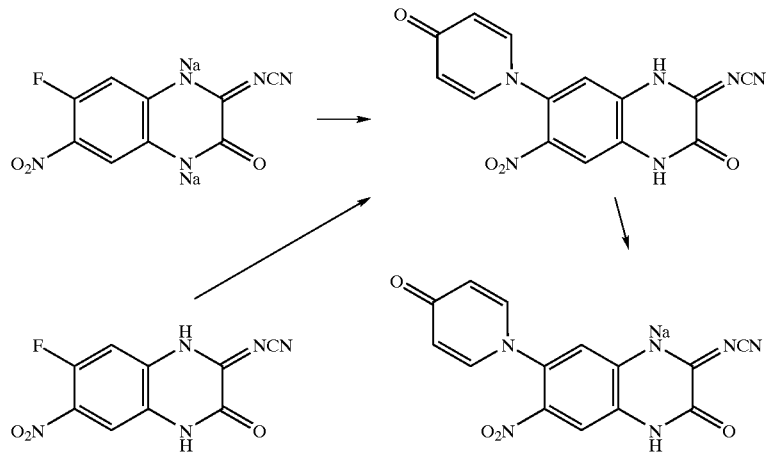

(1) 2-cyanoimino-1,4-dihydro-7-(1,4-dihydro-4-oxo-1-pyridyl)-6-nitro-3-quinoxaline (Method A)
2-Cyanoimino-1,4-dihydro-7-fluoro-6-nitro-3-quinoxaline disodium salt 1.47 g obtained in Example 1(2) and 4-hydroxypyridine were added to DMSO 7 mL and the mixture was stirred at 130° C. for 3 hr. Water 30 mL was added to the mixture under ice-cooling, to which 1N HCl was added to adjust the pH to 3. The precipitation was collected by filtration and washed with water and acetone, then suspended into DMF 15 mL and the mixture was stirred under heating at 120° C. for 30 min. The mixture was collected by filtration, washed with DMF and acetone, and dried, to give the title compound 1.19 g.

mp: >300° C.

Elementary analysis for $C_{14}H_8N_6O_4$

Calcd.: C, 51.86; H, 2.49; N, 25.94 (%)

Found: C, 51.71; H, 2.75; N, 25.84 (%)

$^1$H-NMR ($d_6$-DMSO+$d_5$-pyridine) δ: 6.23 (2H, d, J=7.8 Hz), 7.31 (1H, s), 7.79 (2H, d, J=7.8 Hz), 7.95 (1H, s).

(Method B)

To a solution of 2-cyanoimino-1,4-dihydro-7-fluoro-6-nitro-3-quinoxaline 249 mg obtained in Example 1(3) in DMSO 2.5 mL, were added 4-hydroxypyridine 190 mg and powder KOH (purity 86%) 130 mg at room temperature. The mixture was heated at 120° C. for 2 hr and allowed to stand for cooling, then poured into ice water containing 1N HCl 1.6 mL. The precipitation was collected by filtration and washed with water and acetone. The obtained solid was suspended into DMF 3 mL with stirring at 120° C. and allowed to stand for cooling, then the mixture was collected by filtration and washed with acetone, to give the title compound 205 mg.

(2) 2-cyanoimino-1,4-dihydro-7-(1,4-dihydro-4-oxol-pyridyl)-6-nitro-3-quinoxaline monosodium salt The compound 1.62 g obtained in above (1) was dissolved into the mixed solution of 0.1N NaOH 50 mL and water 150 mL. The obtained solution was evaporated to dryness below 50° C., and the residue was suspended into a mixture of water 10 mL and i-PrOH 20 mL, collected by filtration, and washed with i-PrOH, to give the title compound 1.61 g.

mp: >300° C.

Elementary analysis for $C_{14}H_7N_6NaO_4 \cdot 2H_2O$

Calcd.: C, 43.99; H, 2.90; N, 21.98; Na, 6.01; $H_2O$, 9.43 (%)

Found: C, 43.65; H, 3.17; N, 21.90; Na, 6.01: $H_2O$, 10.02 (%)

$^1$H-NMR ($d_6$-DMSO) δ: 6.14 (2H, d, J=7.8 Hz), 7.22 (1H, s), 7.73 (2H, d, J=7.8 Hz), 7.90 (1H, s), 11.9 (1H, br).

EXAMPLE 3

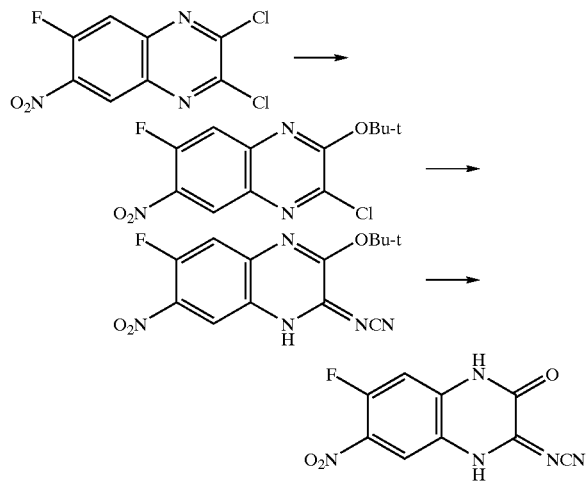

(1) 2-tert-butoxy-3-chloro-7-fluoro-6-nitroquinoxaline

To a solution of 2,3-dichloro-6-fluoro-7-nitroquinoxaline 5.24 g in tetrahydrofran (50 mL), was added dropwise a solution of potassium tert-butoxide 2.51 g in tert-butanol 60 mL at −10 to −8° C. for about 1 hr. After the addition, the mixture was stirred at 0° C. for 1 hr, to which toluene 100 mL and a solution of 0.1M sodium dihydrogen phosphate 20 mL were added, then which was poured into a separatory funnel. The organic layer was washed with water and saturated saline, dried over $MgSO_4$, and evaporated under reduced pressure. The residue was purified with silica gel column (120 g, toluene:hexane=1:1), to give the title compound (pale yellow crystal) 4.19 g.

mp: 141–143° C.

$^1$H-NMR ($d_6$-DMSO) δ: 1.71 (9H, s), 8.03 (1H, d, $J_{HF}$=12.2 Hz), 8.73 (1H, d, $J_{HF}$=7.8 Hz).

(2) 2-tert-butoxy-3-cyanoimino-7-fluoro-6-nitro-4H-quinoxaline

Sodium halide (60% suspension in oil) 80 mg was washed with dried hexane, then which was suspended into dimethylformamide 5 mL. Sodium cyanamide 128 mg, which was prepared from cyanamide and sodium methoxide, was added thereto with stirring at room temperature. Further, 2-tert-butoxy-3-chloro-7-fluoro-6-nitroquinoxaline 600 mg obtained in the above-described (1) was added thereto below 0° C. and the mixture was warmed slowly to 15° C. to generate hydrogen gas moderately. After the termination of the gas, the reaction mixture was poured into a mixture of 1N HCl 2.5 mL, ice water, and ethyl acetate, then which was transferred to a separatory funnel. The organic layer was washed with a saturated saline, dried over $MgSO_4$, and evaporated. The obtained residue was purified with silica gel column (50 g), and the portion eluted with methanol/chloroform(1:20) gives the title compound (ocher powder) 404 mg.

mp:161–164° C.

$^1$H-NMR ($d_6$-DMSO) δ: 1.68 (9H, s), 7.80 (1H, d, $J_{HF}$=12.2 Hz), 8.32 (1H, brs).

(3) 2-cyanoimino 1,4-dihydro-6-fluoro7-nitro3-quinoxaline

To a suspension of 2-tert-butoxy-3-cyanoimino-7-fluoro-6-nitro-4H-quinoxaline 1526 mg obtained in the above-described (2) in ethyl acetate 20 mL, was added dropwise a solution of 4N hydrogen chloride/ethyl acetate (1.5 mL) under ice-cooling. The mixture was warmed to room temperature, stirred for 30 min, and ice-cooled again. The mixture was collected by filtration and washed with cooled ethyl acetate. The obtained residue was added to a mixture of ice water and ethyl acetate, then which was extracted with ethyl acetate. The extract was washed with water and a saturated saline, dried over $MgSO_4$, and evaporated to dryness. The obtained residue was suspended in a mixture of ethyl acetate and chloroform (1:4), then which was warmed to 60° C., allowed to cool, and collected by filtration, to give the title compound (yellow powder) 752 mg.

mp: >300° C.

Elementary analysis for $C_9H_4N_5O_3F$

Calcd.:C, 43.39; H, 1.62; N, 28.11; F, 7.62 (%).

Found:C, 43.29, H, 1.82, N, 27.86, F, 7.35 (%).

$^1$H-NMR ($d_6$-DMSO+NaOD/$D_2O$) δ: 6.69 (1H, d, $J_{HF}$=14.4 Hz), 7.70 (1H, d, $J_{HF}$=8.6 Hz).

EXAMPLE 4

2-cyanoimino-1,4-dihydro-6-(1,4-dihydro-4-oxo-1-pyridyl)-7-nitro-3-quinoxaline potassium salt

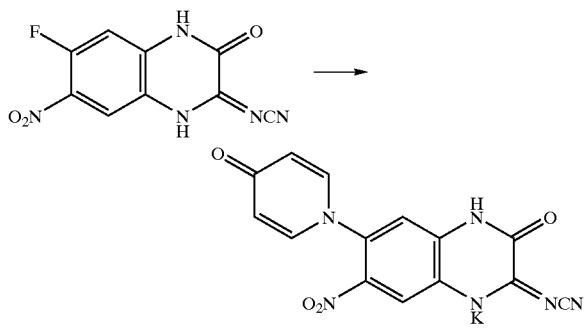

To a solution of 2-cyanoimino-1,4-dihydro-6-fluoro7-nitro-3-quinoxaline 249 mg obtained in Example 3(3) in dimethylsulfoxide 2 mL, were added 4-hydroxypyridine 190 mg and powder KOH (86%) 136 mg with stirring at 120° C. for 3 hr. After cooling, ethanol 6 mL was added thereto, and the precipitaion was collected by filtration. The obtained solid was suspended in a mixture of water and ethanol (1:3) 12 mL, which was warmed to 60° C. and allowed to cool, then collected by filtration. The obtained product 153 mg was dissolved into water, and purified with column using Sephadex® G-10, to give the title compound (ocher powder) 75 mg.

mp: >300° C.

Elementary analysis for $C_{14}H_7N_6O_4K$ $1.5H_2O$

Calcd.:C, 43.19; H, 2.59; N, 21.58; K, 10.04; $H_2O$, 6.93 (%)

Found:C, 43.54; H, 2.78, N, 21.78; K, 9.90; $H_2O$, 7.23(%)

$^1$H-NMR ($d_6$-DMSO) δ: 6.16 (2H, d, J=7.6 Hz), 7.05 (1H, s), 7.78 (2H, d, J=7.6 Hz), 7.87 (1H, s), 12.08 (1H, brs).

EXAMPLE 5

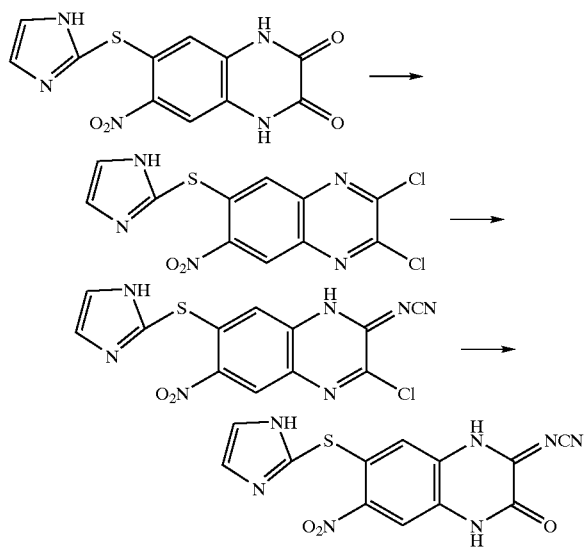

(1) 2,3-dichloro-6-(2-imidazolylthio)-7-nitroquinoxaline

Phosphorus oxychloride 6 mL was added to 1,4-dihydro-6-(2-imidazolylthio)-7-nitro-2,3-quinoxaline-2,3-dione 305 mg which was prepared according to the method used in Example 1 of JP-A 8-59660, with stirring at 105° C. for 4.5 hr. The mixture was evaporated to dryness, to which toluene 5 mL was added, then evaporated again to dryness. To the obtained mixture was added ice water with stirring. The obtained mixture was collected by filtration, and the residual solid was dissolved into dimethylformamide, then which was combined with the filtrate, followed by extraction with chloroform several times. The extract was washed with water, dried over $MgSO_4$, and evaporated. The residue was washed with ethyl acetate, to give the title compound (pale yellow crystal) 263 mg.

mp: >300° C.

$^1$H-NMR ($d_6$-DMSO) δ: 7.10 (1H, s), 7.47 (2H, s), 8.97 (1H, s).

(2) 2-chloro-3-cyanoimino-6-(2-imidazolylthio)-7-1H-nitroquinoxaline

To a solution of 2,3-dichloro-6-(2-imidazolylthio)-7-nitroquinoxaline 120 mg obtained in the above-described (1) in N,N-dimethylformamide 1.5 mL, were added sodium cyanamide 24 mg and sodium hydride (60% suspension in oil) 15 mg under ice-cooling and stirring for 1 hr. The mixture was poured into a mixed solution of 1N HCl 0.73 mL and ice water 10 mL, then the precipitation was collected by filtration, washed with water, i-propyl ether, and dried under heating, to give the title compound (orange powder) 116 mg.

mp: >300° C.

$^1$H-NMR ($d_6$-DMSO) δ: 6.44 (1H, s), 7.88 (1H, s), 8.55 (1H, s).

(3) 2-cyanoimino-1,4-dihydro-7-(2-imidazolylthio)-6-nitro-3-quinoxaline

A solution of 2-chloro-3-cyanoimino-6-(2-imidazolylthio)-7-nitro-1H-quinoxaline 153 mg obtained in the above-described (2) dissolved in 1N NaOH 4 mL was stirred at 50° C. for 30 min. Under ice-cooling, 1N HCl 4 mL and ice water were added thereto to adjust the pH 2–3, then the precipitation was collected by filtration, and washed with water and acetone. The obtained product was crystallized from N,N-dimethylformamide/water to give the title compound (brown powder) 90 mg.

mp: >300° C.

Elementary analysis for $C_1H_7N_7O_3S$

Calcd.:C, 43.77; H, 2.14; N, 29.77; S, 9.74 (%).

Found:C, 43.74; H, 2.32; N, 29.35; S, 9.68 (%)

$^1$H-NMR ($d_6$-DMSO+NaOD/$D_2O$) δ: 6.20 (1H, s), 7.26 (2H, d), 7.79 (1H, s).

EXAMPLE 6

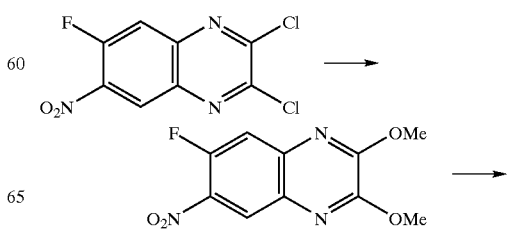

19

-continued

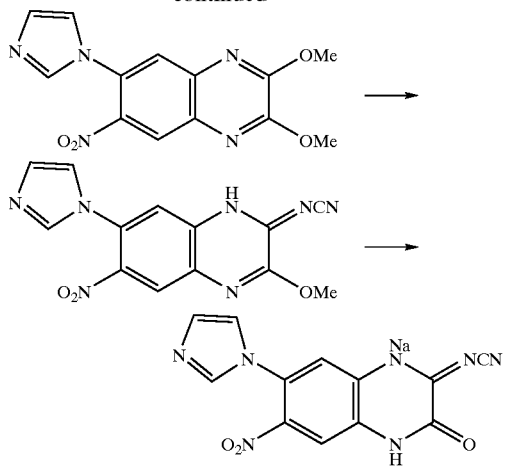

(1) 2,3-dimethoxy-6-fluoro-7-nitroquinoxaline

To a solution of sodium methoxide which was prepared from dried methanol 75 mL and metallic sodium 1.332 g, was added 2,3-dichloro-6-fluoro-7-nitroquinoxaline 4.778 g under ice-cooling and the mixture was stirred at room temperature for 1 hr. The reaction mixture was poured into ice water, then the resulting precipitation was collected and washed with water. The aqueous layer was extracted with chloroform, then the combined product was purified with alumina column chromatography and crystallized from acetone/hexane, to give the title compound (white crystal) 3.342 g.

mp: 137–139° C.

$^1$H-NMR (CDCl$_3$) δ: 4.17 (3H, s), 4.19 (3H, s), 7.58 (1H, d, J$_{HF}$=11.6 Hz), 8.49 (1H, d, J$_{HF}$=7.4 Hz).

(2) 2,3-dimethoxy-6-(1-imidazolyl)-7-nitroquinoxaline

To a solution of imidazole 1.362 g in dimethylsulfoxide 25 mL, was added sodium hydride (60% suspension in oil) 607 mg and the mixture was stirred at room temperature for 1 hr. 2,3-Dimethoxy-6-fluoro-7-nitroquinoxaline 2.533 g described above (1) was added thereto and the mixture was reacted at room temperature for 1 hr. Ice water was added to the reaction mixture, which was neutralized with 5N HCl, then the resulting precipitation was collected by filtration and washed with water. The obtained product was purified with silica gel column chromatography to give the title compound (yellow crystal) 1.005 g.

mp: 160–162.5° C.

$^1$H-NMR (d$_6$-DMSO) δ: 4.11 (6H, s), 7.12 (1H, brs), 7.48 (1H, brs), 7.98 (2H, brs), 8.48 (1H, brs).

(3) 2-cyanoimino-1,4-dihydro-7-(1-imidazolyl)-6-nitro-3-quinoxaline sodium salt.

To a solution of sodium hydride (60% suspension in oil) 280 mg in dimethylformamide 10 mL, was added cyanamide 146 mg under ice-cooling and stirring for 30 min. 2,3-Dimethoxy-6-(1-imidazolyl)-7-nitroquinoxaline 970 mg described above (2) was added thereto and the mixture was reacted for 6 hr. To the reaction mixture were added toluene 20 mL, water 40 mL, and 1N HCl 3.6 mL with stirring for 30 min, then which was separated. The resulting yellow aqueous layer was evaporated to dryness and the residue was dried under reduced pressure to give yellow solid 1.392 g (2-cyanoimino-3-methoxy compound). The product was added to 1N sodium hydroxide 20 mL without purification and the mixture was stirred at 80° C. for 80 min. The reaction mixture was ice-cooled, followed by adding acetic acid 2.5 mL, then which was adjusted to pH 4–5. The orange precipitation was collected by filtration, washed with water and methanol, and dried under reduced pressure to give crude product 666 mg. The product was dissolved into 0.1N sodium hydroxide 22.4 mL and water 40 mL under heating, to which active carbon was added, then the mixture was collected by filtration. The filtrate was evaporated to the weight of about 8 g, to which isopropanol 8 mL was added to stand still. The precipitation was collected by filtration, dried at 100° C. under reduced pressure, and allowed to stand at room temperature to achieve hygroscopicity equilibrium, whereby the title compound (orange powder) 547 mg was obtained.

mp: 296–303° C. (decomp.)

Elementary analysis for C$_{12}$H$_6$N$_7$O$_3$Na 1.5H$_2$O

Calcd.: C, 41.63; H, 2.62; N, 28.32; Na, 6.64; H$_2$O, 7.81 (%)

Found: C, 41.66; H, 2.67; N, 28.03; Na, 6.89; H$_2$O, 7.03 (%)

$^1$H-NMR (d$_6$-DMSO) δ: 7.03 (1H, brs), 7.10 (1H, brs), 7.36 (2H, brs), 7.84 (1H, brs).

EXAMPLE 7

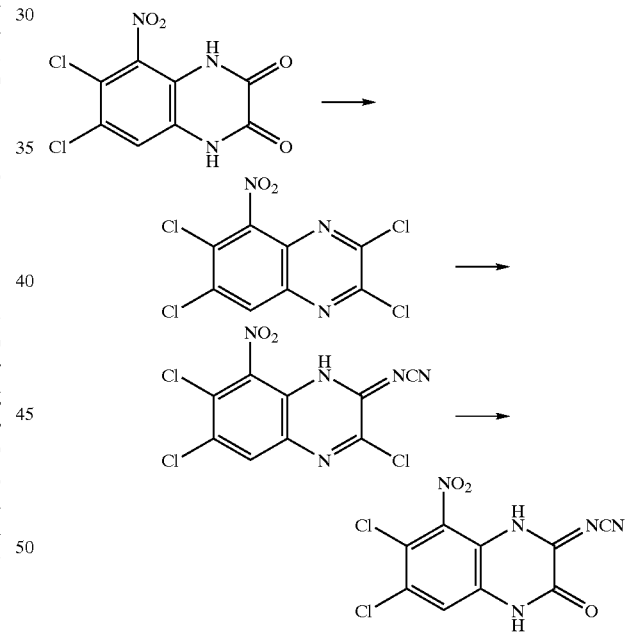

(1) 5-nitro-2,3,6,7-tetrachloroquinoxaline

To 6,7-dichloro-1,4-dihydro-8-nitro-2,3-quinoxalinedione 1.932 g, were added thionyl chloride 14 mL and DMF 0.14 mL with and the mixture was refluxed for 2 hr. The reaction mixture was evaporated to dryness, and toluene 5 mL was added thereto with further evaporation to dryness; these procedures were recycled 3 times. The residue was dissolved into chloroform, which was washed with ice water, water and a saturated saline, and dried over MgSO$_4$. The solvent was evaporated and the obtained solid was crystallized from toluene/hexane to give the title compound (white crystal) 1.59 g.

mp: 118–120 °C.

$^1$H-NMR (d$_6$-DMSO) δ: 8.85 (1H, s).

(2) 2-cyanoimino-8-nitro-3,6,7-trichloro-1H-quinoxaline

To sodium hydride (60% suspension in oil) 40 mg washed with hexane in N$_2$, were added DMF 2 mL and successively sodium cyanamide 64 mg at room temperature. The mixture was ice-cooled and 5-nitro-2,3,6,7-tetrachloroquinoxaline 312 mg obtained above (1) was added thereto and the mixture was stirred below 10° C. for 2 hr. The reaction mixture was poured into ice water containing 1N HCl 1.5 mL and the precipitation was collected by filtration with water. The obtained product was purified with column chromatography using silica gel 10 g, and crystallized with acetone from the portion eluted with chloroform/methanol (10:1), to give the title compound (yellow crystal) 110 mg.

mp: 245–255° C.

$^1$H-NMR (d$_6$-DMSO) δ: 8.11 (1H, s).

(3) 2-cyanoimino-6,7-dichloro-1,4-dihydro-8-nitro-3-quinoxaline

2-Cyanoimino-8-nitro-3,6,7-trichloro-1H-quinoxaline 318 mg obtained above (2) was suspended into 2N sodium hydroxide 10 mL and the mixture was stirred at 50° C. for 10 min. The obtained solution was ice-cooled, and 1N HCl 20 mL and ice water were added thereto to adjust the pH 3–4, then which was extracted with acetic acid. The extract was washed with water and a saturated saline, dried over MgSO$_4$, and evaporated to dryness. The residue was crystallized with acetone/isopropanol to give the title compound (white crystal) 180 mg.

mp: >300° C.

Elementary analysis for C$_9$H$_3$N$_5$O$_3$Cl$_2$

Calcd.: C, 36.03; H, 1.01; N, 23.34; Cl, 23.63 (%).

Found: C, 35.99, H, 1.18, N, 23.25, Cl, 23.40 (%).

$^1$H-NMR (d$_6$-DMSO) δ: 8.45 (1H, s), 9.47 (1H, brs), 9.61 (1H, brs).

EXAMPLE 8

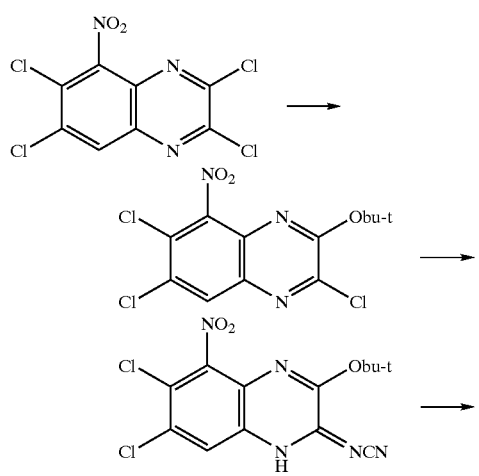

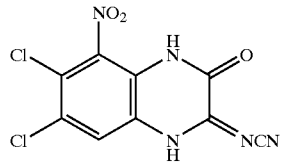

(1) 2-tert-butoxy-8-nitro-3,6,7-trichloroquinoxaline

To 5-nitro-2,3,6,7-tetrachloroquinoxaline 1608 mg obtained in Example 7(1), was added dropwise a solution of potassium tert-butoxide 644 mg in tert-butanol (15 mL) at −5 to 0° C. The reaction mixture was stirred at 0° C. for 30 min, and toluene 50 mL, 0.1 M sodium dihydrogen phosphate 5 mL, and water were added thereto with shaking. The organic layer was separated, washed with water and saturated saline, and dried over MgSO$_4$. After evaporation, the residue was subjected to column chromato (silica gel/toluene) and crystallized from acetone, to give the title compound (colorless crystal) 1092 mg.

mp: 173–175° C. (decomp.)

$^1$H-NMR (d$_6$-DMSO) δ: 1.61 (9H, s), 8.58 (1H, s).

(2) 2-tert-butoxy-3-cyanoimino-6,7-dichloronitro-4H-quinoxaline

To a suspension of sodium hydride (60% suspension in oil) 40 mg in DMF 2.5 mL, was added monosodium cyanamide 64 mg at room temperature. The mixture was cooled to −10° C., and 2-tert-butoxy-8-nitro-3,6,7-trichloroquinoxaline 351 mg described above (1) was added thereto with slowly warming to 0° C., followed by stirring for 2 hr. Ice water was added to the reaction mixture, which was made about pH 6 with 1N HCl 1 mL, and extracted with ethyl acetate. The extract was washed with water and saturated saline, and dried over anhydrous MgSO$_4$. After evaporation, the residue was washed with chloroform, and crystallized from acetone and toluene, to give the title compound (pale yellow crystal) 279 mg.

mp: 276–280° C. (decomp.)

$^1$H-NMR (d$_6$-DMSO) δ: 1.60 (9H, s), 8.00 (1H, s).

(3) 2-cyanoimino-6,7-dichloro-1,4-dihydro-5-nitro-3-quinoxalinone

To a suspension of 2-tert-butoxy-3-cyanoimino-6,7-dichloro-nitro-4H-quinoxaline 103 mg obtained in the above-described (2) in chloroform 2 mL, was added trifluoroacetic acid 0.4 mL under ice-cooling. After stirring for 15 min, the mixture was evaporated to dryness, then the residue was dissolved into ethyl acetate, washed vigorously with ice water, water, and saturated saline, and dried over anhydrous MgSO$_4$. After evaporation, the residue was washed with chloroform, and crystallized from acetone and ethyl acetate, to give the title compound (white crystal) 39 mg.

mp: 280–285° C.

Elementary analysis for C$_9$H$_3$N$_5$O$_3$Cl$_2$

Calcd.:C, 36.03; H, 1.01; N, 23.34; Cl, 23.63 (%).

Found:C, 36.30, H, 1.22, N, 23.19, Cl, 23.16(%).

$^1$H-NMR (d6-DMSO) δ: 8.40 (1H, s), 9.47 (2H, brs).

EXAMPLE 9

2,3-bis(cyanoimino)-6,7-dichloro-2,3-dihydro-5-nitroquinoxaline

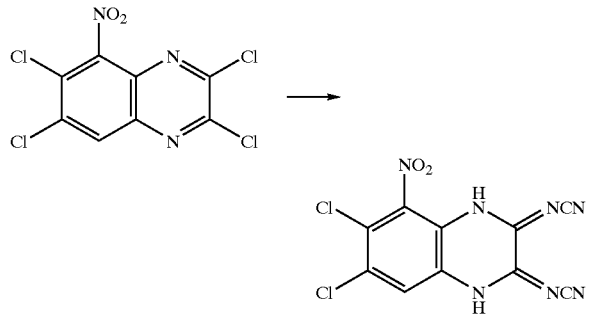

Sodium halide (60% suspension in oil) 48 mg was washed with hexane and suspended into DMF 2 mL. To the suspension were added monosodium cyanamide 77 mg, and then 5-nitro-2,3,6,7-tetrachloroquinoxaline 156 mg of Example 7(1) under ice-cooling. The mixture was stirred for 1 hr, which was warmed to room temperature with further stirring for 2 hr. The resultant mixture was ice-cooled and ice water 10 mL was added thereto. After extraction with ethyl acetate to remove neutral and basic materials, the remained aqueous layer was made pH6 with 1N HCl and further extracted with ethyl acetate. The combined extract was washed with water and saturated saline, dried over anhydrous $MgSO_4$, and evaporated. The residue was crystallized from ethanol to give the title compound (pale yellow crystal) 124 mg.

mp: >300° C. (slowly decomp. >100° C.)

Elementary analysis for $C_{10}H_3N_7O_2Cl_2$

Calcd.:C, 37.06; H, 0.93; N, 30.25; Cl, 21.88 (%).

Found:C, 36.92; H, 1.18; N, 29.88; Cl, 21.58 (%).

$^1$H-NMR ($d_6$-DMSO) δ: 8.47 (1/4 H, s), 8.58 (3/4 H, s), 9.63 (2H, brs).

EXAMPLE 10

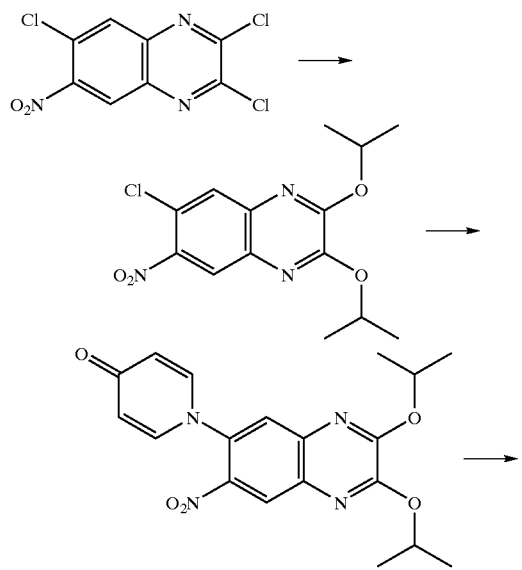

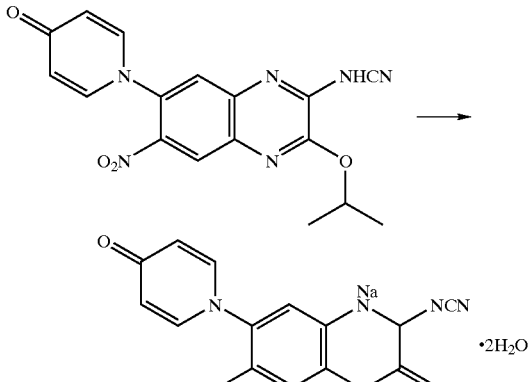

(1) 6-chloro-2,3-diisopropoxy-7-nitroquinoxaline

To a solution of sodium isopropoxide prepared from metallic sodium 4.25 g and dried isopropyl alcohol 200 mL, was added dried tetrahydrofran 30 mL, and further added dropwise a solution of 7-nitro-2,3,6-quinoxaline 18.93 g in dried tetrahydrofran 120 mL at 10 to 15° C. The mixture was stirred at the same temperature for 20 min, then which was poured into an ice-cooled solution of sodium dihydrogen phosphate. The resultant mixture was extracted with toluene, washed with water, dried, and evaporated. The residue was crystallized with isopropyl ether to give the title compound (pale yellow crystal) 19.5 g.

mp: 114–116° C.

$^1$H-NMR ($d_6$-DMSO) δ (ppm): 1.41 (3H×2, d, J=6.2 Hz), 5.48 (2H, m), 8.01 (1H, s), 8.38 (1H, s).

(2) 6-(1,4-dihydro-4-oxo1-pyridyl)-2,3-diisopropoxy-7-nitroquinoxaline

A mixture of 4-hydroxypyridine sodium salt 702 mg, the compound 1.63 g obtained in above described (1), and dried dimethylformamide 3.5 mL was stirred at 125° C. for 3 hr. The resultant mixture was added to an ice-cooled solution of sodium dihydrogen phosphate, then the precipitate was collected by filtration with water. The obtained product was dried and crystallized from acetone to give the title compound (pale brown crystal) 1.02 g.

mp: 217–219° C.

$^1$H-NMR ($d_6$-DMSO) δ (ppm): 1.43 (3H, d, J=6.2 Hz), 1.44 (3H, d, J=6.2 Hz), 5.52 (2H, m), 6.21 (2H, d, J=7.6 Hz), 7.84 (2H, d, J=7.6 Hz), 8.07 (1H, s), 8.51 (1H, s).

(3) 2-cyanoimino-7-(1,4-dihydro-4-oxo-1-pyridyl)-3-isopropoxy-6-nitroquinoxaline To a solution of the compound 769 mg obtained in above described (2) dissolved in a mixture of dried dimethylformamide 7 mL and dried tetrahydrofran 7 mL, was added monosodium cyanamide 256 mg and the mixture was stirred at 50° C. for 3 hr. The mixture was ice-cooled, and ice water 28 mL was added thereto, then which was acidified with 1N HCl to adjust the pH about 4. The precipitate was collected by filtration, washed with water and acetone, and dried to give the title compound (yellow brown crystal) 563 mg.

mp: >300° C.

$^1$H-NMR ($d_6$-DMSO) δ (ppm): 1.40 (3H, d, J=6.2 Hz), 5.44 (1H, septet, J=6.2 Hz), 6.78 (2H, d, J=7.4 Hz), 7.72 (1H, s), 8.33 (2H, d, J=7.4 Hz), 8.36 (1H, s).

(4) 2-cyanoimino-1,4-dihydro-7-(1,4-dihydro-4-oxo-1-pyridyl)-6-nitro-3-quinoxaline monosodium salt To a mixture of the compound 366 mg obtained in the above-described (3) and dried dimethylsulfoxide 5 mL, was added powder sodium hydroxide 412 mg, and the mixture was stirred at 45° C. for 2 hr. The mixture was allowed to stand for cooling, which was neutralized by adding water 5 mL and 5N HCl 1.8 mL, then the mixture was modified to pH 3 to 4 with 1N HCl. The resultant precipitate was collected by filtration, washed with water and acetone, dried, then the obtained product was dissolved into sodium hydroxide 2 ml at room temperature, and 1N HCl was added dropwise to adjust the pH 8. The precipitated crystal was collected by filtration and washed with water and isopropyl alcohol, to give the title compound 170 mg. The physical data was identical with that of the compound obtained in Example 2(2).

Experiment 1 (Receptor Affinity)

As to 2-cyanoimino-1,4-dihydro-7-(1,4-dihydro-4-oxo-1-pyridyl)-6-nitro-3-quinoxaline monosodium salt (hereinafter referred to as compound 2(2)) obtained in Example 2(2), the affinity for the AMPA receptor and glycine-binding site of the NMDA receptor was determined as follows.

(1) AMPA Receptor

Cerebral cortex of Slc-Wistar rat (body weight: 250–300 g) was homogenized with 10 times volume of 30 mM Tris-acetate buffer (pH 7.1) containing 2.5 mM $CaCl_2$, then the mixture was centrifugalized (30,000×g, 15 min) and re-suspended (×3 times). The resultant suspension was restored at −80° C. until use. The froze suspension was thawed at room temperature and suspended into 30 mM Tris-acetate buffer (pH 7.1) containing 2.5 mM $CaCl_2$ and 100 mM KSCN, to give a membrane fraction. The membrane fraction was incubated with 30 nM [$^3$H]AMPA and a test compound of various concentrations at 0° C. for 30 min. The mixture was diluted and collected by filtration with Whatman GF/C filter to terminate the reaction, then the radioactivity of $^3$H remained on the filter was determined with a liquid scintillation counter. The non-specific binding was determined using 1 mM non-radioactive glutamate to calculate the $IC_{50}$ value.

(2) Glycine-binding Site of NMDA Receptor Complex

Cerebral cortex of Slc-Wistar rat (body weight: 250–300 g) was homogenized with 20 times volume of 5 mM Tris-acetate buffer (pH 7.4) containing 1 mM EGTA, 0.1 mM PMSF and 0.01% bacitracin (50,00×g, 30 min) and re-suspended (×4 times). The resultant suspension was restored at −80° C. until use. The froze suspension was thawed at room temperature and incubated at 2° C. in 0.08% triton X-100 solution for 10 min, then the mixture was washed 2 times and suspended into 50 mM Tris-acetate buffer (pH 7.4), to give a membrane fraction. The membrane fraction was incubated with 100 nM [$^3$H]glycine and a test compound of various concentrations at 0° C. for 10 min. The mixture was diluted and collected by filtration with Whatman GF/C paper to terminate the reaction, then the radioactivity of $^3$H remained on the filter was determined with a liquid scintillation counter. The non-specific binding was determined using 1 mM non-radioactive glycine to calculate the $IC_{50}$ value. The results are shown in Table 1.

TABLE 1

| $IC_{50}(\mu M)$ | |
|---|---|
| $^3$H-AMPA | $^3$H-glycine |
| 0.034 | 7.5 |

Experiment 2 (Anticonvulsant Effect on AMPA-induced Seizure)

The anticonvulsant effect of compound 2(2) on AMPA-induced seizure was determined. According to the method described in J. T. Haley and W. G. McCormich, Br. J. Pharmacol. 12, 12–15(1957), AMPA 2 nmol/5 $\mu$L was intracerebroventricular administered to the cerebral ventricle of Slc-ddY mouse (4–5 weeks, male). The test compound, in a volume of 0.1 mL /10 g, was intravenously administered 1 min before the AMPA administration. The convulsion was examined by observing and checking, for 15 min from the AMPA administration, the reveal of jumping, wild-running, chronic convulsion and tonic convulsion, then the $ED_{50}$ value was calculated by Probit method.

(Result)

$ED_{50}$ (mg/kg)=6.9

Experiment 3 (Inhibition Effect on Cerebral Infarction)

As to compound 2(2), the inhibition effect on cerebral infarction was examined. Slc-Wistar rat (14–15 weeks, 294–364 g weight, SLC Japan) had an operation according to the method described in Nagasawa H. and Kogure K., (1989), Stroke 20, 1037–1043. Briefly the animals were anesthetized with halothane (FLUOTHANE, Takeda Chemical Industries Ltd.). After median incision of the neck skin, the right external carotid artery (ECA) was carefully dissected. A coated nylon thread (#4-0, 17.5 mm, Nitcho Kogyo Co. Ltd.) was inserted from the lumen of the ECA to the right internal carotid artery to occlude the origin of the right middle cerebral artery. After surgery, anesthesia was immediately discontinued. The rats exhibit neurological deficits characterized by left-sided hemiparesis and animals not showing hemiparesis were excluded. After 1 hr of MCA occlusion, the thread was removed to allow reperfusion under halothane anesthesia. Body temperature was maintained at 37° C. with a heating pad during ischemic and reperfusion surgery.

The test compound was administered from 15 min after reperfusion for 1 hr by continuous infusion via a catheter (Clay Adams; PE-20) inserted into the femoral vein in a volume of 4 ml/kg/hr.

After 24 hr of reperfusion following 1 hr of MCA occlusion, rat was perfused with physiological saline containing heparin under pentobarbital anesthesia and the brain were removed after decapitation. The brain was cut into 12 coronal sections at 1 mm intervals using tissue chopper (McLWAIN) and immersed in saline containing 2% 2,3,5-triphenyltetrazolium-Cl (Wako Pure Chemical Industries, Ltd.) for 15 min. The stained brain sections were fixed by 10% formalin neutral buffered solution and infarct areas were quantified by an image analyzer system (OPTIMAS, Ver6.0) following scanning (Scantouch210, Nikon). The result is shown in Table 2.

TABLE 2

| Treatment (via intravenous) | Dose (mg/kg/h) | n= | Infarct area at cerebral cortex (% of saline, mean ± standard error) |
|---|---|---|---|
| Saline | 4 | 15 | 100 ± 7.61 |
| compound 2(2) | 0.3 | 8 | 79.55 ± 13.99 |
| | 1 | 9 | 55.99 ± 11.77* |
| | 3 | 8 | 50.34 ± 10.14** |
| | 10 | 5 | 46.71 ± 15.24* |

*p < 0.05, **p < 0.01 (ANOVA-Dunnett's test compared to saline-treated group)

The compound of present invention inhibited dose-dependently the rat's cerebral infarction.

Experiment 4 (Nephrotoxicity)

(Method)

Compound 2(2) was intravenously administered by a bolus of 100 mg/kg to SD rat (9–10 weeks), which was killed 24 hr later. The both-side kidneys were immediately extracted from the rat. After measuring the weight, one kidney was embedded in paraffin to give a tissue preparation. The other kidney was homogenized, then the extract was subjected to liquid chromatography to determine the concentration of compound 2(2).

(Result)

The weight of the kidney has not changed compared to the vehicle group. The kidney tissue had no pathological unusual and compound 2(2) was not detected in the kidney.

Industrial Utility

A compound of the present invention is useful as a preventive or therapeutic agent for various central nervous diseases caused by the binding of excitatory amino acids to NMDA receptors, esp., glycine-binding site and AMPA receptors in central nervous.

What is claimed is:

1. A compound having a quinoxaline partial structure of the formula:

(I)

wherein X and Y each is independently O or NCN, provided that at least one of X and Y is NCN.

2. A compound of the formula:

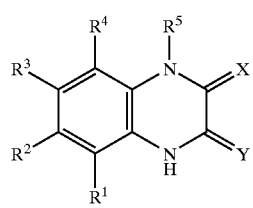

(II)

wherein,

X and Y each is independently O or NCN, provided that at least one of X and Y is NCN;

$R^1$, $R^2$, $R^3$, and $R^4$ each is independently hydrogen, halogen, nitro, cyano, hydroxy, optionally substituted amino, optionally substituted lower alkyl, optionally substituted lower cycloalkyl, optionally substituted lower alkoxy, optionally substituted lower alkylthio, optionally substituted lower alkylcarbonyl, carbamoyl optionally substituted with lower alkyl, carbamoylamino optionally substituted with lower alkyl, sulfamoyl optionally substituted with lower alkyl, sulfamoylamino optionally substituted with lower alkyl, optionally substituted sulfonyl, optionally substituted aryl, optionally substituted heterocyclic group, or optionally substituted heterocyclylthio;

$R^5$ is hydrogen, hydroxy, optionally substituted lower alkyl, optionally substituted lower alkoxy, or optionally substituted lower cycloalkyl;

$R^1$ and $R^2$, $R^2$ and $R^3$, $R^3$ and $R^4$, and $R^4$ and $R^5$, each taken together with the adjacent atoms may form a carbocycle which may be substituted or may contain a heteroatom(s), the pharmaceutically acceptable salt, or the hydrate thereof.

3. The compound of claim 2, wherein X is NCN; Y is O.
4. The compound of claim 2, wherein X is O; Y is NCN.
5. The compound of claim 2, wherein both X and Y are NCN.
6. The compound of claim 2, wherein $R^5$ is hydrogen.
7. The compound of claim 2, wherein X is NCN; Y is O; $R^5$ is hydrogen.
8. The compound of claim 2, wherein $R^1$ is hydrogen, halogen, or nitro.
9. The compound of claim 2, wherein $R^2$ is hydrogen, halogen, nitro, or halogenated lower alkyl.
10. The compound of claim 2, wherein $R^3$ is hydrogen, halogen, nitro, halogenated lower alkyl, optionally substituted heterocyclic group, or optionally substituted heterocyclylthio.
11. The compound of claim 2, wherein $R^4$ is hydrogen, halogen, or nitro.
12. The compound of claim 2, wherein $R^1$ is hydrogen; $R^2$ is hydrogen, halogen, nitro, or halogenated lower alkyl; $R^3$ is hydrogen, halogen, nitro, halogenated lower alkyl, optionally substituted heterocyclic group, or optionally substituted heterocyclylthio; $R^4$ is hydrogen, halogen, or nitro.
13. The compound of claim 2, wherein X is NCN; Y is 0; $R^1$ is hydrogen; $R^2$ is hydrogen, halogen, nitro, or halogenated lower alkyl; $R^3$ is hydrogen, halogen, nitro, halogenated lower alkyl, optionally substituted heterocyclic group, or optionally substituted heterocyclylthio; $R^4$ is hydrogen, halogen, or nitro; $R^5$ is hydrogen.
14. The compound of claim 2, wherein X is NCN; Y is O; $R^1$ is hydrogen; $R^2$ is halogen, nitro, or trihalogenated methyl; $R^3$ is halogen, nitro, trihalogenated methyl, optionally substituted heterocyclic group, or optionally substituted heterocyclylthio; $R^4$ is hydrogen or nitro; $R^5$ is hydrogen.
15. The compound of claim 12, wherein optionally substituted heterocyclic group is 1,4-dihydro-4-oxo-1-pyridyl, 1-imidazolyl or 1-pyrrolyl; heterocyclylthio is 2-imidazolylthio.
16. The compound of claim 2, wherein X is NCN; Y is O; $R^1$ is hydrogen; $R^2$ is nitro; $R^3$ is 4-oxo-1-pyridyl; $R^4$ is hydrogen; $R^5$ is hydrogen, or a pharmaceutically acceptable salt or hydrate thereof.
17. The compound of claim 16, which is a monosodium salt or dihydrate of 2-cyanoimino-1,4-dihydro-7-(1,4-dihydro-4-oxo-1-pyridyl)-6-nitro-3-quinoxaline.
18. A pharmaceutical composition containing a compound described in claim 1.
19. A pharmaceutical composition having an antagonistic effect on glutamate receptors, which contains a compound described in claim 1.
20. A method for treating a disease due to hyperexcitation of glutamate receptors, which comprises administering to a patient in need thereof a compound of claim 1, in an amount effective to treat the disease.
21. The method of claim 20, wherein the disease is Parkinson's disease, senile dementia, Huntington's disease, epilepsy, cerebral infacrtion, stroke, ischemic cerebral disorders, head trauma, spinal cord trauma, anoxia, hypoglycemia, ischemic hyponoia, or ischemic hypokinesis.

22. The method of claim 20, wherein the disease is cerebral infarction.

23. A method for preparing a compound (II-1) of the formula:

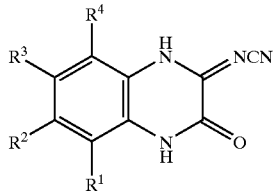

(II-1)

wherein $R^1$, $R^2$, $R^3$ and $R^4$ are independently hydrogen, halogen, nitro, cyano, hydroxy, optionally substituted amino, optionally substituted lower alkyl, optionally substituted lower cycloalkyl, optionally substituted lower alkoxy, optionally substituted lower alkylthio, optionally substituted lower alkylcarbonyl, carbamoyl optionally substituted with lower alkyl, carbamoylamino optionally substituted with lower alkyl, sulfamoyl optionally substituted with lower alkyl, sulfamoylamino optionally substituted lower alkyl, optionally substituted sulfonyl, optionally substituted aryl, optionally substituted heterocyclic group, or optionally substituted heterocyclylthio, which comprises 1) dealkylating $R^6$ in a compound (III-1) of the formula:

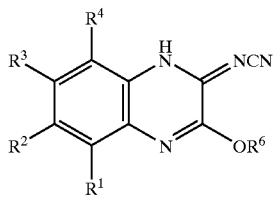

(III-1)

wherein $R^1$, $R^2$, $R^3$ and $R^4$ are the same as defined above; $R^6$ is a hydroxy protecting group, or 2) hydrolyzing Hal in a compound (IV-1) of the formula:

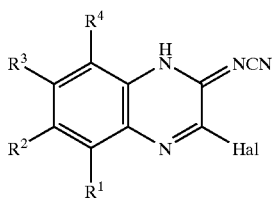

(IV-1)

24. A compound of formula (III-1):

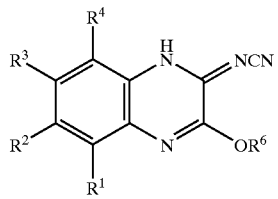

(III-1)

wherein $R^1$, $R^2$, $R^3$ and $R^4$ are independently hydrogen, halogen, nitro, cyano, hydroxy, optionally substituted amino, optionally substituted lower alkyl, optionally substituted lower cycloalkyl, optionally substituted lower alkoxy, optionally substituted lower alkylthio, optionally substituted lower alkylcarbonyl, carbamoyl optionally substituted with lower alkyl, carbamoylamino optionally substituted with lower alkyl, sulfamoyl optionally substituted with lower alkyl, sulfamoylamino optionally substituted lower alkyl, optionally substituted sulfonyl, optionally substituted aryl, optionally substituted heterocyclic group, or optionally substituted heterocyclylthio; and $R^6$ is a hydroxy protecting group.

25. A compound of formula (IV-1):

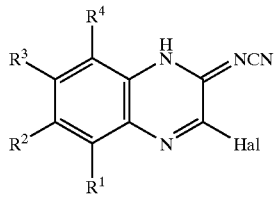

(IV-1)

wherein $R^1$, $R^2$, $R^3$ and $R^4$ are independently hydrogen, halogen, nitro, cyano, hydroxy, optionally substituted amino, optionally substituted lower alkyl, optionally substituted lower cycloalkyl, optionally substituted lower alkoxy, optionally substituted lower alkylthio, optionally substituted lower alkylcarbonyl, carbamoyl optionally substituted with lower alkyl, carbamoylamino optionally substituted with lower alkyl, sulfamoyl optionally substituted with lower alkyl, sulfamoylamino optionally substituted lower alkyl, optionally substituted sulfonyl, optionally substituted aryl, optionally substituted heterocyclic group, or optionally substituted heterocyclylthio; and Hal is halogen.

* * * * *